United States Patent [19]

Osborne

[11] 4,332,158
[45] Jun. 1, 1982

[54] SLUMP TESTING DEVICE

[76] Inventor: Howard S. Osborne, 1965 Rainbow Ridge, P.O. Box 1691, Corona, Calif. 91720

[21] Appl. No.: 148,541

[22] Filed: May 9, 1980

[51] Int. Cl.³ .......................................... G01N 11/14
[52] U.S. Cl. .................................. 73/59; 73/861.71
[58] Field of Search ................ 73/54, 861.71, 861.74, 73/59

[56] References Cited

U.S. PATENT DOCUMENTS

| | | | |
|---|---|---|---|
| 1,125,017 | 1/1915 | Green | 73/59 |
| 1,730,893 | 10/1929 | Lichtenberg | 73/59 X |
| 2,013,837 | 9/1935 | Perry | 73/54 X |
| 2,629,790 | 2/1953 | Laing et al. | 200/52 |
| 2,821,079 | 1/1959 | Kerridge | 73/54 |
| 3,027,756 | 4/1962 | Head | 73/53 |
| 3,098,384 | 7/1963 | Nusbaum | 73/861.74 |
| 3,147,612 | 9/1964 | Evans | 73/53 |
| 3,330,269 | 7/1967 | Pieper | 73/861.71 X |
| 3,364,730 | 1/1968 | Wall | 73/59 X |
| 3,474,663 | 10/1969 | Whitmer et al. | 73/54 |
| 3,631,712 | 1/1972 | Mercier | 73/54 |
| 3,640,121 | 2/1972 | Mercier | 73/54 |
| 3,881,354 | 5/1975 | Block | 73/861.71 |
| 3,924,447 | 12/1975 | Garrison | 73/54 |
| 4,148,215 | 4/1979 | Hofstetter, Jr. | 73/54 |

Primary Examiner—Daniel M. Yasich
Attorney, Agent, or Firm—Poms, Smith, Lande & Rose

[57] ABSTRACT

A manually held device for measuring and indicating slump of flowing concrete material being discharged from a concrete mixer along a discharge chute in which a torque responsive member is contained within a manually held housing, a sensing assembly is connected to the torque responsive member and extends beyond the housing for at least partial immersion in concrete material flowing in a discharge chute. The sensing assembly includes diametrically opposite sensing members of different size adapted to turn about the axis of the torque responsive member to produce torque forces of different magnitude and direction, the resultant of said forces being transmitted to the torque responsive member, and indicating means on said housing and associated with the sensing assembly for showing measurement of the slump or consistency of the flowing concrete material. A method of measuring and indicating the consistency of a concrete mass by positioning a sensing means in the flowing mass of concrete material with the axis of the sensing means generally normal to the flow direction of the concrete material and applying resultant torque forces imparted to the sensing means by the flowing concrete material to a torque transmitting means, and indicating the magnitude of the resultant torque force on a scale calibrated in terms of inches of slump.

17 Claims, 6 Drawing Figures

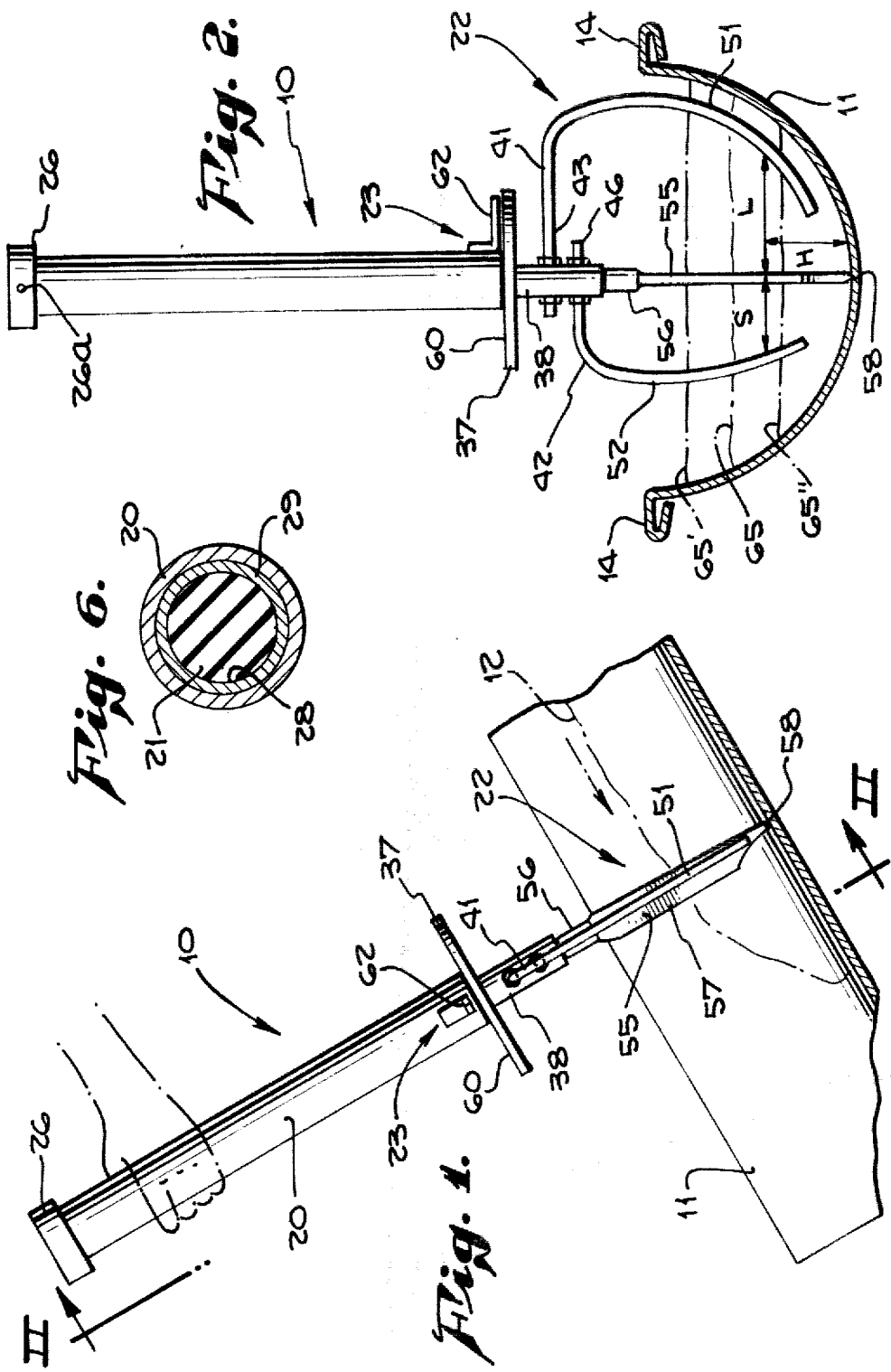

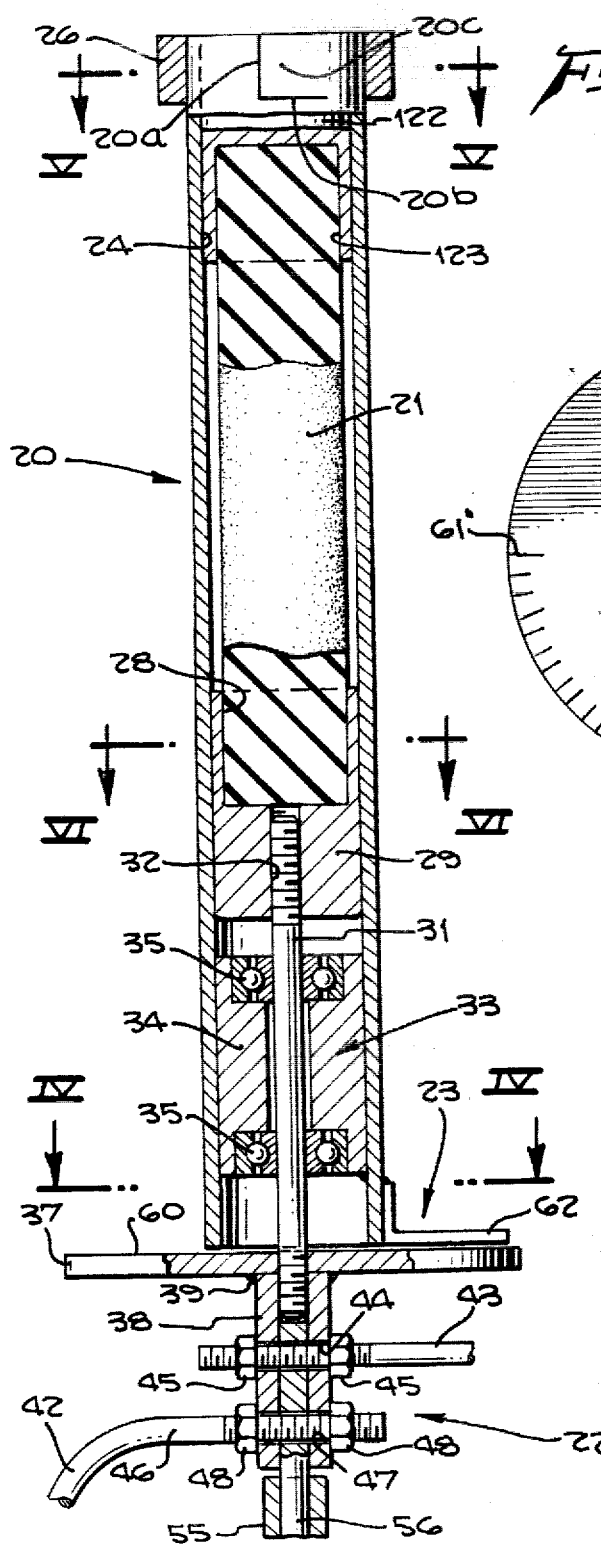
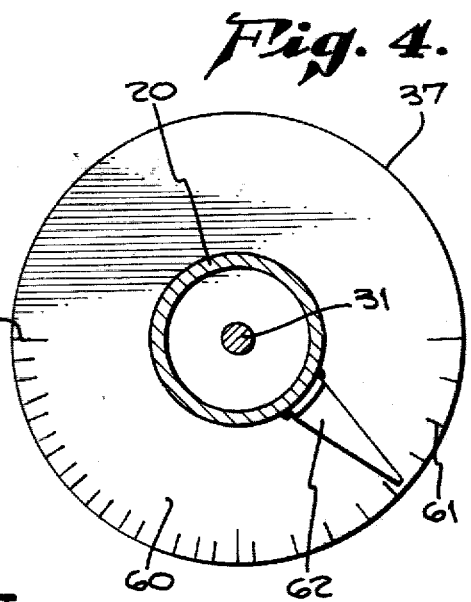
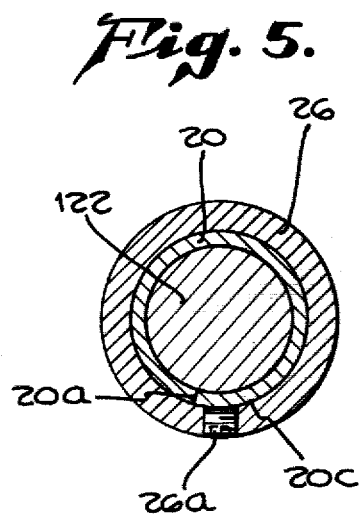

SLUMP TESTING DEVICE

BACKGROUND OF THE INVENTION

In order to maintain quality control of fresh concrete as delivered to a job site and to determine compliance with specifications under which the concrete is furnished, usual testing procedures require the taking of samples of the concrete material as it is delivered from the concrete mixer. The concrete samples are used for compression test cylinders and also for measuring the consistency or slump of the delivered concrete material.

The handling of such samples of concrete material for conducting such tests are set forth by the American Society for Testing Materials in their specifications ANSI/ASTM C 172-171 and the standard test method for slump of concrete in ANSI/ASTM C 143-78. ASTM methods require that two samples be taken from the center portion of the load over a period not to exceed 15 minutes. These two samples are then to be combined and reconstituted; i.e., thoroughly mixed with a shovel in a wheel-barrow to assure uniformity, the test to be started within five minutes and completed within two and one-half minutes. A probable elapsed time of 20± minutes by which time the truck may be completely discharged providing no timely basis for rejection and therefore no control of the load in question and only vague correlation with the next succeeding loads.

It will be apparent that determining the slump in this manner as it has been done for approximately 50 years or more provides slump data available to the quality control person on the job only after the load has been placed in its final location or form. There is little opportunity at the conclusion of testing to redirect the discharge flow of the concrete or modify the mixture of the concrete material being delivered, since the load being tested is often easily discharged by the time the test has been made. If the delivered concrete material does not meet the slump specified, remedial steps must be taken on succeeding loads based on still further testing.

It will be apparent that job sites impose various conditions upon the manner in which ready mixed concrete material can be delivered to its final location. Such conditions often make the taking of samples of the concrete in accordance with ASTM specifications difficult and sometimes cause serious interruption of the concreting operations. To obtain indication of the slump of concrete being delivered, it has been proposed that measurement of slump of the concrete be taken by devices placed on the mixing drum to measure the consistency of the concrete material within the drum. Such prior proposed devices are shown in U.S. Pat. Nos. 2,821,079, 1,730,893, 2,013,837, 3,640,121 and 3,924,447.

Other prior proposed devices for controlling consistency of a flowable material have included a vane or a blade insertable into a flow path of material, the vane or blade being connected to a torsion means mounted outside of the conduit or receptacle in which the material was moving. Such prior devices are shown in U.S. Pat. Nos. 3,364,730, 4,148,215, 2,629,790, 3,147,612 and 3,027,756.

SUMMARY OF INVENTION

The present invention relates to a portable, manually operable slump testing device for rapidly measuring the consistency or slump of concrete flowing along a path. The invention particularly relates to a manually held device for measuring and indicating slump of flowing concrete without taking samples of the concrete or interrupting the activities of the concreting crew.

The primary object of the present invention is to provide a manually operable slump testing device adapted to quickly and accurately determine the consistency or slump of concrete.

An object of the invention is to provide such a testing device adapted for use without interrupting concreting operations and readily adapted to provide multiple slump readings during unloading operations of each truck or of several trucks.

Another object of the invention is to provide a testing device for measuring and indicating the consistency of a flowable material in which the device automatically compensates for changes in rate of flow of the material and changes in density of the material.

Another object of the invention is to provide a single testing device which is accurate, reliable, and is convenient to use, as well as being readily cleaned and maintained.

A further object of the invention is to provide a testing device or concrete feeler which does not require samples as such to be taken and replaces the slump cone, rod, wheelbarrow, scoop, shovel, and tape measure.

The present invention contemplates a slump testing device which is readily adapted to the convenience and requirements of the practical man in the field such as a superintendent, architect's representative, laboratory inspector, or quality control engineer. The testing device of this invention generally comprises a torque responsive means adapted to be manually held, a sensing assembly operatively connected to the torque responsive means and adapted to be positioned in a particular manner in a flowing stream of concrete material, and indicator means connected to the sensing means and to the torque responsive means for visually directly indicating the inches of slump of the concrete material into which the sensing means is positioned.

The present invention also contemplates a method of measuring and indicating consistency of a flowable material by positioning a sensing means in the flowing material with the axis of the sensing means generally perpendicular or normal to the flow direction of the material, the sensing means applying a torque and a countertorque to a torque responsive means in a predetermined ratio, and indicating resultant torque forces on a readily observable indicia scale.

The invention particularly contemplates a device for determining the consistency of a material under material flow conditions wherein a sensing means is connected to a torque responsive member and includes spaced sensing elements of different size providing torque and countertorque forces of different magnitude acting about the axis of the torque responsive member.

A still further object of the invention is to provide on the testing device an indicia arrangement for providing one or more sets of indicia for indicating slump of several types or compositions of concrete including concrete with additives to enhance viscosity during pouring of the load.

Various other objects and advantages of the present invention will be readily apparent to those skilled in the art from the following description of the drawings in which an exemplary embodiment of the invention is shown.

IN THE DRAWINGS

FIG. 1 is a side elevational view, partly in section, of a slump testing device embodying this invention, the device being shown in operble position in a discharge chute of a ready-mix concrete truck, the discharge chute being shown partly in section.

FIG. 2 is a front view of the device shown in FIG. 1 and taken from the plane indicated by line II—II of FIG. 1, the discharge chute being shown in section.

FIG. 3 is an enlarged fragmentary sectional view of the device shown in FIG. 1, the section being taken in a plane bisecting the device.

FIG. 4 is a sectional view taken from the plane indicated by line IV—IV of FIG. 3.

FIG. 5 is a sectional view taken in the plane indicated by line V—V of FIG. 3.

FIG. 6 is a sectional view taken in the plane indicated by line VI—VI of FIG. 3.

In FIG. 1 a measuring and indicating device for determining consistency of flowing concrete is generally indicated at 10. Device 10 is shown in association with a discharge chute 11 inclined for gravity flow of concrete material from a ready-mix truck, not shown. The lower end of chute 11 is associated with suitable means for conveying the concrete material to its desired location, such conveying means not being shown. It will be understood that the angle of inclination of the discharge chute 11 is exemplary only and depending upon the site conditions, the inclination of the chute may be greater or less. Chute 11 guides a concrete mass 12 along a path and the depth of the concrete mass may vary. Generally the depth of concrete flowing along such a path may be about 7" deep at the center line of the chute. The chute 11 is generally of a semi-cylindrical cross section with reinforced edges 14.

Slump indicating device 10 generally comprises an elongated cylindrical housing 20, a torque responsive member 21 contained within housing 20, a sensing assembly 22 extending beyond the lower end of housing 20 and indicating means for the amount of slump or consistency of the concrete material generally indicated at 23.

Housing 20 may comprise an elongated, hollow, metal cylinder or tube of selected diameter, such as 1½ or 2 inches and of selected length such as a 1½ or 2 feet. Housing 20 may be readily grasped by the hands of a user.

Within housing 20 is torque responsive member 21, which in this example may comprise an elongated elastomeric cylindrical member of less outer diameter than the inner diameter of housing 20 to provide ample clearance between the sides of member 21 and the internal surfaces of housing 20. At the upper end of torque member 21, a mounting block 122 has a recess 123 tightly and frictionally engaging the upper end of member 21. Block 122 is provided with a relatively tight, snug, sliding fit at 24 with the inner surfaces of the upper end of housing 20. The upper end of housing 20 may be provided with a longitudinal saw cut 20a joined with a transverse saw cut 20b to provide a tab 20c adapted to be forced radially inwardly to tightly, yet adjustably, secure the housing in relation to the block 122. Such securement includes an external collar 26 provided with a threaded port having a set screw 26a adapted to be positioned opposite and against tab 20c so that as the set screw 26a is tightened, tab 20c is deflected radially inwardly into tight, secure, frictional engagement with block 122 which is secured in fixed relation to the torque responsive means 21. Relative movement between the upper end of torque member 21 and housing 20 is thereby prevented while providing adjustment of the relative rotative or turned positions of the housing with respect to the torque responsive means upon loosening the set screw for a purpose later described.

The lower end of torque member 21 is similarly closely fitted within a recess 28 provided on a lower mounting block 29. Recess 28 tightly and snugly frictionally engages the lower end portion of torque member 21 to prevent relative rotation between mounting block 29 and the torque member 21. Mounting block 29 has an outer diameter sufficiently less than the inner diameter of housing 20 to permit relative, free, rotational movement between block 29 and housing 20.

It will be understood that the securement of blocks 122 and 29 to opposite ends of the torque responsive member 21 is exemplary only and that other methods of securing these parts in assembled relation may be used. For example, each end of the torque responsive member may be of slightly reduced diameter to receive and accommodate a brass tubing which may be slipped over each end and adhesively bonded to the tube. The brass tubing has a length adapted to receive at least a portion of the associated block 122 or 29, the brass tubing being sweat soldered to the steel block.

Sensing assembly 22 is associated with the torque responsive member 21 by an axially disposed shaft 31 having threaded engagement 32 with an axial bore in block 29. Shaft 31 is rotatably antifrictionally mounted within the lower end of housing 20 by bearing means 33 including an elongated bearing housing 34 fitted within housing 20 and carrying at opposite ends thereof ball bearing means 35. Shaft 31 extends beyond the lower end of housing 20 and has threaded connection with a circular indicia plate 37 and with a tubular fitting 38 extending below plate 37 and welded thereto as at 39.

Sensing assembly 22 includes a sensing member 41 and a sensing member 42 disposed in a plane passing through the axis of shaft 31 and of housing 20 and secured to fitting 38. In this example upper horizontal end portion 43 of sensing member 41 extends through transverse diametrical holes 44 in fitting 38. Upper portion 43 may be threaded to permit lateral adjustment of sensing member 41 and securement thereof in selected position by nuts 45 on opposite sides of fitting 38. Sensing member 42 is similarly provided with an upper horizontal portion 46 which extends through diametrically aligned transverse openings 47 in fitting 38. Lateral position of sensing element 42 is adjusted and secured by threads on portion 46 and adjustment nuts 48.

The larger sensing member 41 is provided with a curved sensing element 51 which is shaped to generally conform to the curvature of the inner surface of chute 11. Sensing element 51 is generally uniformly spaced from the interior surface of chute 11 when in operable position and such space is at least greater than 1½" which is usually the maximum size for large aggregate in a concrete mix. Space between sensing element 51 and the chute 11 must be sufficient to permit the largest aggregate of a concrete mix to readily pass therethrough without interference from or with sensing element 51. It will be apparent from the construction of sensing member 41 that lateral adjustment to provide such spacing of member 41 is readily obtained by the manner in which the upper portion 43 is connected to the fitting 38.

Sensing member 42 is provided with a curved sensing element 52 which because of the size of sensing member 42 is relatively widely spaced from the interior surfaces of chute 11 and aggregate of maximum size, such as 1½", will readily pass by. The curvature of sensing element 52 is specifically related to the curvature of sensing element 51 with respect to the location of the sensing elements 51 and 52 to the projected axis of shaft 31, torque member 21 and housing 20. As best seen in FIG. 2, at any selected height H above the center line of chute 11 the lateral spacing S of an incremental portion of small sensing element 52 will be approximately one-half the lateral spacing L of the corresponding horizontally opposite increment of sensing element 51 from the axis. Such proportionate spacing of sensing elements 52 and 51 from the projected axis of shaft 31 is maintained from the bottom of the sensing elements 51, 52 to a height which corresponds to the top of the reinforced edges of chute 11. Thus, for whatever depth of flow of concrete material that may be in chute 11, the response of sensing elements 51, 52 to the flow of material will be in the same proportion.

Sensing members 41 and 42 may be made of suitable metal rod stock and are of the same diameter so that the flat plate area of an increment of sensing element 51 or 52 will be virtually the same.

A positioning and stabilizing member 55 extends along the prolonged axis of shaft 31 and is rotatably mounted on an extension 56 carried by fitting 38. Such rotatable fitting is only schematically shown and may be of any suitable construction such as a relatively loose threaded fitting. The positioning and stabilizing member is blade-like in configuration and has a trailing fin 57 adapted to move downstream of the flow of concrete and to offer little flow resistance thereto while providing sufficient strength for positioning and supporting device 10 in the chute. The bottom end 58 of the positioning member 55 is preferably hardened and pointed so that when the device 10 is used in a chute 11 the pointed end may slightly indent the metal of the chute to hold against displacement the lower end of member 55 in a selected position on the chute.

Indicating means for showing the inches of slump or consistency of the concrete material comprises the upper face 60 of circular plate 37 which is provided with indicia 61 in spaced relation to indicate inches and fractions of inches of slump. Housing 10 has secured to it an indicator pointer or needle 62 which is secured to housing 10 in any convenient manner and fixed thereto for showing relative movement between housing 21 and sensing assembly 22, specifically plate 37 and pointer 62. Indicia 61 has a reference indicia which is aligned with pointer 62 under no torque conditions of torque member 21.

Indicia 61 (FIG. 4) is provided along the edge of one quadrant of the plate 37. When the device is initially assembled, housing 20 which fixedly carries the pointer 62 may be turned relative to the torque sensing means 21 while the set screw 26a is retracted so that the tab 20c does not bear against mounting block 122. In relaxed position, pointer 62 may lie at the indicia 61 provided on the radius at one edge of the quadrant. After the pointer 62 is so aligned, set screw 26a may be tightened and tab 20c urged radially inwardly into tight frictional contact with the block 122.

During normal use of the slump testing device, as described immediately hereafter, the pointer 62 and the quadrant with which it is initially aligned move relative to one another within the quadrant. In some compositions of concrete in which certain additives have been mixed, the viscosity of the concrete is increased to facilitate pouring and discharge from the ready mix truck without disturbing or affecting the water-cement ratio which determines strength of the concrete. In one such additive presently used in the mixing of concrete, the viscosity of the discharged concrete is substantially increased, although when the concrete is in its final location, the viscosity may rapidly change to that which would normally be measured in a standing slump test. In order to measure the slump of such a modified composition concrete containing such an additive, it is desirable that another quadrant of plate 37 be so calibrated with indicia 61' so that the reading on the testing device is correlated or calibrated to the actual slump of the concrete while actually measuring the increased viscosity of the concrete mixture being poured. Thus, when the testing device of this invention is used for measuring this type of concrete, the set screw is retracted and the indicator 62 and plate 37 relatively moved so that the indicator 62 is at the beginning of the selected differently calibrated quadrant. Thus, a direct reading may be made of the viscosity of the modified concrete mixture and the indicia 61' are so calibrated that the reading directly taken therefrom may be in terms of the slump of the concrete. It will be apparent that the remaining two quadrants of plate 37 may be similarly provided with indicia calibrated for other types of concrete compositions. The invention also contemplates that the face of plate 37 may be provided with an adaptor containing calibrated indicia for other types of concrete compositions in the event the number of types of concrete exceed four, which would normally occupy the four quadrants of plate 37.

Operation of the slump testing device 10 includes the grasping of the housing 20 by the hands of the user and positioning the device at right angles to the path of flow of the concrete material in the chute 11. The concrete material flowing in the chute is usually about 7" deep as indicated by line 65, although in some conditions the depth of the concrete material may be as high as line 65' or as low as line 65". To stabilize device 10 in such normal relation to the chute and concrete flow, the point 58 is jabbed or sharply pressed into the bottom surface of chute 11 so that the pointed end 58 can be held against displacement along the flow path. The positioning of the device 10 normal to such flow requires only visual determination of such right angle or normal relationship. The positioning and stabilizing member 55 with its fin 57 presents a narrow edge to the flow of concrete and the fin tends to further stabilize the positioning member in the flowing concrete.

Since the positioning and stabilizing member 55 is rotatably mounted in fitting 38, the sensing assembly 22 has unrestrained movement relative to the member 55. As the flowing concrete material passes sensing assembly 22, the concrete material exerts a force on sensing elements 51 and 52. The force exerted upon sensing element 51 is a function of the flat plate area of sensing element 51 which is immersed in the concrete material. Since the immersed portion of element 51 is spaced a distance from the axis of the device, a moment of force is created which has a moment arm determined by the distance of the incremental portions of element 51 from the axis of the device. Such moment of force is transmitted to the fitting 38 and tends to rotate fitting 38, shaft 31 and plate 37 in one direction, in this instance the sensing element 51 is displaced downstream of the flow path.

At the same time sensing element 52 reacts in substantially the same manner as sensing element 51, except that the moment arm of incremental flat plate areas of sensing element 52 immersed in the concrete material from the axis of the device is approximately one-half that of the moment arm and moment of force exerted on fitting 38 by element 51. The moment of force provided by sensing element 52 is counter to that of sensing element 51, but because of the shorter moment arm S, the moment of force exerted by sensing element 52 tends to cancel only approximately one-half of the moment of force exerted by sensing element 51. Thus, the sensing element 52 would be displaced upstream of the flow path. The different sizes of elements 51, 52 and the difference in length of moment arms S and L produce torque and countertorque forces of different magnitude.

The resultant of the moment of forces exerted by sensing elements 51 and 52 on shaft 31 is transmitted to the torque responsive member 21 and if such resultant turning force is not resisted by the person handling the device 10, the housing 20 will turn until the sensing elements are disposed at right angles to a plane transverse and normal to the chute 11. The operator of the device determines the measurement of the consistency of the concrete material or its slump by applying a manual counterforce to housing 20 until the sensing assembly is disposed in a transverse plane at right angles to the chute 11 as shown in FIGS. 1 and 2. Thus, the amount of torque which the torque responsive member 21 absorbs is indicated by the position of indicator pointer 62 with respect to the indicia 61 on plate 37. The indicia are calibrated in terms of inches and fraction of inches so that the amount of slump is directly read from the indicating means.

It will be apparent that the positioning of device 10 in the flow of concrete material and the application of the torque forces by the concrete material to the sensing assembly and the application of countertorque forces manually by the operator to the housing 20 requires less than a minute and the slump of the material is immediately directly read. Slump readings may be rapidly taken at different times during the flow of a batch of concrete material from the ready-mix truck, if desired, or may be taken continuously if so desired. Furthermore, if more than one ready-mix truck is discharging concrete at the same time at a job site, the device 10 may be readily used in each of the discharge chutes of such mixing trucks and the slump of concrete being delivered by the several trucks can be almost immediately determined.

The relationship of the moment arms S and L remain approximately the same as the height H of the concrete material changes. Thus, the sensing assembly 22 will respond to the consistency of the flowing concrete material during variations in height of the flowing concrete mass. The sensing elements 51 and 52 are diametrically disposed and are positioned in a transverse plane to the chute during a reading, the velocity of the flowing concrete material across such transverse plane is approximately the same. Changes in velocity of the flow of concrete at different times during the taking of a slump reading will be automatically compensated for by the counter acting moments of force, the resultant of which is transmitted to the torque responsive member 21.

The arrangement of the sensing elements 51, 52 of the sensing assembly 22 also compensate for any changes in density of the concrete material flowing past device 10. In this respect well-mixed concrete discharged from a ready-mix truck has or should have a uniform consistency so that when the flowing mass is placed at a job site, the concrete in the form or slab will be of relatively uniform consistency in order to develop the desired and specified strength characteristics.

After the device has been used, concrete particles adhering to the sensing assembly and stabilizing member may be readily removed by washing with a stream of water from a water hose which is usually readily available at the truck.

In this example of the invention, the sensing assembly 22 is described as having a moment arm ratio of about 2:1. This ratio or proportion may be readily changed by the manner in which the sensing members 41 and 42 are mounted in the tubular fitting 38. Such change in ratio would require recalibration of the indicia on the plate 37. Use of a maximum moment arm L on one side of the sensing assembly is preferable in that the size of the sensing element 51 can be minimized while still providing sufficient flat plate area to create a torque force. It will be understood that a minimal sized sensing element 51 and 52 will provide less interference with the flowing mass of concrete material in which there may be aggregate of a size from $1\frac{1}{2}"$ and less. The moment arm ratio and the size of the sensing element 51 and 52 may be varied depending upon the type of flow material being measured as to its consistency.

It will be understood that various changes and modifications may be made in the construction of a slump testing device as described above and all such changes and modifications coming within the spirit of this invention and within the scope of the appended claims are embraced thereby.

I claim:

1. A manually held device for measuring and indicating slump of flowing concrete being discharged from a concrete mixer along a discharge chute, comprising in combination:

an elongated housing;

an elongated torque responsive member within said housing, one end of said responsive member being fixed to said housing;

a sensing assembly connected to the other end of said torque responsive member within said housing for rotation about the axis of said torque responsive member and extending beyond said housing;

said sensing assembly beyond said housing including at least two diametrically opposite sensing members of different size adapted to produce torque forces of different direction and magnitude when said sensing assembly is inserted into said flowing concrete, the resultant of said forces being transmitted to said torque responsive member;

an indicator element on said housing;

and indicia associated with said sensing assembly and movable relative to said indicator element in response to the resultant of said forces to show measurement of slump.

2. A device as stated in claim 1 wherein said torque responsive member includes an elongated elastomeric cylindrical member.

3. A device as stated in claim 1 including bearing means in said housing for mounting said sensing assembly.

4. A device as stated in claim 1 wherein
said sensing members have curved elements proportionately spaced about a prolongation of said axis of said torque responsive member.

5. A device as stated in claim 4 wherein
said sensing members include rods of uniform cross sectional area.

6. A device as stated in claim 1 including
a positioning and stabilizing member extending between said sensing members and having an end adapted to contact the bottom wall surface of the discharge chute.

7. A device as stated in claim 1 including
means for fixing one end of said torque responsive member with respect to said housing and including
a radially inwardly deformable tab on said housing, and
means for pressing said tab radially inwardly into frictional contact with said torque member.

8. A device as stated in claim 7 wherein
said tab on said housing is formed by a longitudinal slot and a transverse slot in the end portion of the housing.

9. A device as stated in claim 7 including
an external collar on said end portion of said housing, and a set screw carried by said collar for urging said tab radially inwardly.

10. In a method of quickly obtaining measurement of the consistency of a flowing concrete mass without interrupting such flow in which a sensing assembly includes a pair of sensing elements on opposite sides of and nonsymmetrically arranged with respect to an elongated positioning member, comprising the steps of:
positioning said sensing assembly in said flowing mass and with said sensing elements and said positioning member in normal relation to the flowing mass for developing torque and countertorque forces of different direction and magnitude;
transmitting the difference of said torque forces to a torque responsive member;
and measuring the amount of torque imparted to said torque responsive member for indicating consistency of the concrete mass.

11. A method as stated in claim 10 wherein said nonsymmetrically arranged pair of sensing elements lie in a plane, and wherein the step of simultaneously positioning said sensing elements includes the step of
positioning the plane of said pair of elements transversely to and perpendicularly to the flow path.

12. A method as stated in claim 10 wherein said torque responsive member includes an end portion fixed to a housing and wherein the step of transmitting the difference of said torque forces to the torque responsive member includes the step of
holding said housing and fixed end portion of said torque responsive means against rotational forces imparted thereto by said sensing elements.

13. In a device for determining consistency of material under material flow conditions along a path, the combination of:
torque responsive means;
a positioning member;
a sensing means associated with said positioning member and connected to said torque responsive means to transmit torque forces thereto, said sensing means being adapted to be positioned normal to and in the flow of material along said path;
said sensing means including spaced sensing elements on opposite sides of said positioning member, said sensing elements being of different sizes providing torque and countertorque forces of different magnitude, the resultant of said forces being transmitted to said torque responsive means;
and indicator means responsive to said forces and cooperably connected to the sensing means and to the torque responsive means for indicating consistency of the flowing material.

14. In a device as stated in claim 13 wherein the sensing means includes
one sensing element spaced a selected distance from said positioning member and adapted to be spaced from a wall defining said path, and a second sensing element spaced from said positioning member a distance less than the first sensing element.

15. In a device as stated in claim 14 wherein
said first and second sensing elements converge at a selected rate towards each other and said axis.

16. In a device for measuring consistency of a flowable material including sand, cement and liquid as the material flow along a path defined by a wall, the combination of:
a longitudinal member adapted to contact a wall of said path;
a material sensing means comprising a first sensing element carried by such longitudinal member and having a sensing portion in spaced relation to said member and of a selected size,
and a second sensing element carried by said longitudinal member and having a sensing portion spaced from said member opposite to said first sensing portion and having a reduced size,
a torque responsive means connected with said member and sensing means to receive the resultant force imparted to said sensing elements by the material flowing along said path,
said torque responsive means including a portion adapted to be held against rotation;
and means cooperably associated with said sensing means and said torque responsive means for indicating the consistency of the flowing material.

17. A device as stated in claim 16 wherein said sensing elements lie in a plane diametrical with respect to said longitudinal member,
and said sensing elements are positionable in said path with said plane transverse and vertical to the flow path.

* * * * *